United States Patent [19]

Liberda et al.

[11] 4,098,819
[45] Jul. 4, 1978

[54] PROCESS FOR THE PRODUCTION OF PHOSPHORIC ACID-DIMETHYLAMIDE-DICHLORIDE OR PHOSPHORIC ACID-BIS-(DIMETHYLAMIDE)-CHLORIDE

[75] Inventors: Heinz Liberda; Hellmuth Spes; Alfred Trommet, all of Burghausen, Fed. Rep. of Germany

[73] Assignee: Wacker-Chemie GmbH, Munich, Fed. Rep. of Germany

[21] Appl. No.: 747,574

[22] Filed: Dec. 6, 1976

[30] Foreign Application Priority Data

Dec. 23, 1975 [DE] Fed. Rep. of Germany ....... 2558185

[51] Int. Cl.$^2$ ................................................ C07F 9/26
[52] U.S. Cl. .................................................. 260/543 P
[58] Field of Search ...................................... 260/543 P

[56] References Cited

FOREIGN PATENT DOCUMENTS 2,421,124  1/1975  Fed. Rep. of Germany.
1,030,836  5/1966  United Kingdom ............. 260/543 P

OTHER PUBLICATIONS

Houben–Weyl, "Methoden der Org. Chem.," Band XII/2, Tal 2, pp. 383–385, 445–449 (1964).

*Primary Examiner*—Norman Morgenstern
*Attorney, Agent, or Firm*—Allison C. Collard

[57] ABSTRACT

Process for the production of phosphoric acid-dimethylamide-dichloride (A) or phosphoric acid-bis-(dimethylamide)-chloride (B) by reacting phosphorus oxychloride and dimethylammonium chloride at elevated temperature under anhydrous conditions, which comprises heating phosphorus oxychloride with a mixture of dimethylammonium-chloride and A and/or B to temperatures of 130° to 240° C, using per mole of phosphorus oxychloride at least 1 mole of dimethylammonium chloride and optionally distilling off A or B from the reaction mixture. The compounds A and B produced according to the process are valuable intermediate products for the manufacture of pesticides, solvents, and lubricants.

12 Claims, No Drawings

PROCESS FOR THE PRODUCTION OF PHOSPHORIC ACID-DIMETHYLAMIDE-DICHLORIDE OR PHOSPHORIC ACID-BIS-(DIMETHYLAMIDE)-CHLORIDE

The invention relates to a process for the production of phosphoric acid-dimethylamide-dichloride, in the following called A, and the production of phosphoric acid-bis-(dimethylamide)-chloride, in the following called B.

The production of the above products is known, per se, but the known processes are not satisfactory.

Thus, for example, phosphoric acid-dimethylamidedichloride (A) can be obtained by reacting phosphorus oxychloride with dimethylamine is stoichiometric amounts in which dimethylammonium chloride is produced as a by-product. Since the reaction is strongly exothermic, it is necessary for the reactants to be very dilute, i.e., the reaction must be carried out in the presence of an inert solvent and at temperatures of about 0° C in order to achieve a satisfactory selectivity. It is possible to use instead of the free amine dimethylammonium chloride, but this reaction is very slow, so that it is necessary to use a large excess of phosphorus oxychloride and the reaction mixture has to be heated under reflux of the phosphorus oxychloride for at least 8-10 hours. The two processes may, furthermore, be combined, the ammonium chloride formed from phosphorus oxychloride and free amine being reacted at elevated temperature with excess phosphorus oxychloride after distilling off the solvent (cf. "Methoden der organischen Chemie" by Houben-Weyl, Vol, XII/2, 4th Edition, pages 383–385; Inorganic Synthesis, Volume 7, pages 69–71 (1963).

To produce phosphoric acid-bis-(dimethylamide)-chloride (B), again phosphorus oxychloride can be reacted with dimethylamine in stoichiometric amounts. In this case, too, large quantities of solvent and low temperatures are required, and furthermore, the dimethylammonium chloride must, if possible, be removed completely before the distillation of the end product since at elevated temperature, it acts as a catalyst to the decomposition of Compound B. This method may also be carried out as a two-stage process, according to which first of all Compound A is produced according to one of the above-mentioned methods, advantageously isolated in pure form and subsequently further reacted with dimethylamine, it being possible, if desired, to reuse the dimethylammonium chloride freed from the solvent for the production of A (cf. loc. cit. pages 445–447; Inorganic Synthesis, page 72).

Compound B may furthermore be obtained by reacting phosphoric acid-tris-(dimethylamide) with phosphorus oxychloride in the molar ratio of 2 : 1 at elevated temperature, a transfer of the amide groups taking place to form B (cf. loc. cit. page 449).

A further general method for producing phosphoric acid diamidechlorides by reacting phosphorus oxychloride with the hydrochlorides of secondary amines at elevated temperature or a variation thereof, according to which phosphorus oxychloride is reacted with 2 moles of an amine to form phosphoric acid-amide dichloride and the mixture of this with the aminohydrochloride simultaneously formed is heated without solvent, elevated temperatures being necessary in each case (cf. loc. cit., pages 448–449), cannot be used for the production of Compound B and has also not been described expressis verbis, since, as already mentioned, dimethylammonium chloride acts under these conditions as a catalyst to the decomposition of Compound B. This opinion is also confirmed by the statements concerning the State of the Art on page 2, paragraph 2, of German Offenlegungsschrift No. 2,421,124, where it is stated that the procedure of binding several amino groups to the phosphoryl group by reacting phosphoric acid halides with aminohydrochlorides cannot be considered in the case of thermally sensitive starting compounds and end compounds, volatile amines or sublimable aminohydrochlorides.

Not one of the known processes is satisfactory, however, for being carried out on a large industrial scale, since for this, either — when using the free amine — expensive apparatus is required for cooling, salt separation and distillation of large amounts of solvent, or — when using the amine salt — long periods of heating are necessary and large amounts of the excess reactant have to be distilled, and in addition to this, the last-mentioned process can be used only for the production of A, whereas in the splitting of phosphoric acid-tris-(dimethylamide), according to which Compound B is obtainable, this starting material must first of all itself be produced from phosphorus oxychloride and dimethylamine by way of A and B as intermediate stages.

The object of the invention is, therefore, to provide a process which, starting from dimethylammonium chloride, which is produced as a by-product in numerous reactions of dimethylamine with replaceable chlorine atoms, renders possible in a simple and economic manner both the production of Compound A and of Compound B in good yields without expensive filtration devices, redistillation plants and/or long heating periods being necessary.

The process according to the invention for the production of phosphoric acid-dimethylamide-dichloride A or phosphoric acid-bis-(dimethylamide)-chloride B by reacting phosphorus oxychloride and dimethylammonium chloride at elevated temperature under anhydrous conditions is characterized in that phosphorus oxychloride is heated with a mixture of dimethylammonium chloride and A and/or B to temperatures of 130° to 240° C, wherein there is used per mole of phosphorus oxychloride at least 1 mole of dimethylammonium chloride, and optionally A or B is distilled off from the reaction mixture.

The process according to the invention is based on the surprising discovery that Compound B can be produced from Compound A by reaction with the amine salt, contrary to existing opinion, and Compound A can be obtained, more advantageously than by the hitherto known methods, by a route via B by reaction with phosphorus oxychloride which has not been described hitherto. These reactions are illustrated by the following equations, in which Me in each case signifies a methyl group:

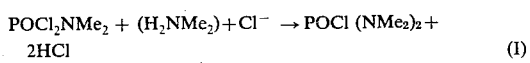

When carrying out the process according to the invention, to produce Compound A, the molar amount of amine salt used must at least correspond to the molar amount of phosphorus oxychloride, that is to say, at least one mole of dimethylammonium chloride must be present per mole of phosphorus oxychloride, while to produce Compound B, theoretically, at least two moles of dimethylammonium chloride are necessary per mole of phosphorus oxychloride. In both cases, the phosphorus oxychloride reacts with B to form A according to equation (II), while the B thus consumed is continuously reformed from A and amine salt according to equation (I), this reaction being the slower of the two and therefore determinative of the speed of the entire operation. When using phosphorus oxychloride and amine salt in the molar ratio 1 : 1, the reaction stops when the phosphorus oxychloride used is completely consumed to yield A. When using phosphorus oxychloride and amine salt in the molar ratio of 1 : 2, on the other hand, after complete consumption of phosphorus oxychloride, Compound A reacts further with the amine salt still present to form B, whereby when the evolution of hydrogen chloride is complete, the reaction stops.

The fact that the reaction according to equation (II) proceeds extremely rapidly renders possible the operation at the high temperatures of the given range. Preferably, the process according to the invention is carried out at temperatures of 160° to 210° C, operation at the reflux temperature of A (approximately 190° C) having proved particularly suitable. By controlling the rate of addition of phosphorus oxychloride at the rate at which it is consumed, this is prevented from being present in excess at any point during the reaction, and causes the operating temperature to drop as a result of reflux.

At temperatures higher than approximately 160° C, the amine salt dissolves almost completely in the reactants A and/or B, so that the process according to the invention can be carried out in the preferred temperature range in homogeneous phase. In addition, provision can be made for thorough mixing of the reactants by mechanical motion. This is not absolutely necessary, however, since the reaction mixture is well mixed by the hydrogen chloride being evolved and optionally by the reflux of A, even without stirring.

The ratio of the quantity of dimethylammonium chloride to that of the reactants A and/or B is of no decisive importance. Generally, approximately 1.5-5 parts by weight of A and/or B can be used per part by weight of dimethylammonium chloride.

The amine salt either may be present from the beginning or may be metered in during the reaction. Preferably, the amine salt is added in the molten state as a result of which its handling is much simplified. There is used as starting material, for example, the amine salt resulting as a by-product, in the form of a solvent-moist solid or an aqueous solution, of the reaction of dimethylamine with replaceable chlorine atoms. When using the solvent-moist solid, heating to the melting point, optionally in vacuo, is sufficient to remove the residual solvent. The amine salt can be obtained in the molten form, likewise in simple manner, from the aqueous solution, for example, by evaporating a portion of the preferably saturated solution and melting the residue. This melt continuously has further solution added to it as a result of which the water evaporates rapidly. Once the supply of solution has ended residual moisture is removed in vacuo. The production of the melt is advantageously undertaken in the same reaction vessel that is subsequently used for carrying out the process according to the invention. As a result, expensive and time-consuming measures, such as crystallizing out, precipitating or spray-drying, which are usually necessary for obtaining solid, dry amine salt, are dispensed with.

The decisive feature in carrying out the process according to the invention is that at least one of the reactants A or B must be present right at the beginning of the reaction. The initial ratio of the quantities of the two reactants A and B can vary within wide limits. The higher the proportion of A, the more the reaction according to equation (I) which consumes the amine salt is promoted. If using pure A, it is advantageous to heat the mixture of A and amine salt for a short time at the reaction temperature before adding the phosphorus oxychloride and then to add the phosphorus oxychloride slowly, that is, at the rate at which it is consumed by the formation of B for the reaction according to equation (II). If using pure B, on the other hand, the phosphorus oxychloride can be added very rapidly without preheating the mixture of B and amine salt since upwards of approximately 130°, it is immediately consumed by the B already present for the reaction according to equation (II).

For carrying out the process according to the invention, it is, however, advantageous to use mixtures of A and B, mixtures of approximately equal parts by weight of A and B having proved particularly suitable.

Such mixtures can be produced, for example, by heating A with less than the stoichiometrically equivalent quantity of dimethylammonium chloride necessary for the formation of B according to equation (I), or by heating B with less than the stoichiometrically equivalent quantity of phosphorus oxychloride necessary for the formation of A according to equation (II). Mixtures of this type can also be obtained by a variation of the known process for the production of B from phosphoric acid-tris-(dimethylamide) in which the latter is heated with more than the stoichiometrically equivalent quantity of phosphorus oxychloride necessary therefor. This process is advantageously carried out by introducing phosphorus oxychloride into phosphoric acid-tris-(dimethylamide) which has been preheated to 150°-190° C, 1.5-3 moles of phosphorus oxychloride being used per 2 moles of phosphoric acid-tris-(dimethylamide).

There are preferably used per part by weight of amine salt at least 4 parts by weight of a mixture of approximately equal parts by weight of A and B, so that at least 2 parts by weight of A are present per part by weight of amine salt. An excess of A in relation of the amine salt used is particularly advantageous since, by this means, the reaction can be controlled by the reflux of A, and complete dissolution of the amine salt is guaranteed. Furthermore, the tendency of the amine salt to sublime does not cause any interference since quentities of salt sublimed in the condenser are returned to the reaction mixture by the refluxing of A.

When using stoichiometrically exactly equivalent amounts of phosphorus oxychloride and amine salt with the inclusion of the respective quantities of A and/or B, the process proceeds quantitatively, wherein in each case A or B results as residue whose further purification is superfluous if using very pure starting materials.

It is not, however, absolutely necessary to carry out the process for the production of A or B until the quantity of amine salt used is in each case completely consumed since unreacted amine salt does not interfere in the separation by distillation of A if this is carried out in vacuo at vessel temperatures of below 100° C, and B can easily be separated from the remaining reactants by fractionation. In addition, unconsumed quantities of A or B can each be used again for further mixture.

To produce Compound A, the process according to the invention is preferably carried out in such a manner that the phosphorus oxychloride is introduced at the rate at which it is consumed into a mixture of dimethylammonium chloride and approximately equal parts by weight of A and B, wherein there are present per mole of phosphorus oxychloride at least 1 mole of dimethylammonium chloride and at least 1 mole of A, the reaction mixture is heated under reflux until the evolution of hydrogen chloride is practically complete, and subsequently the majority of the A formed is distilled off from the reaction mixture under reduced pressure. This process can be carried out continuously, the phosphorus oxychloride and the dimethylammonium chloride being introduced in the molar ratio of 1 : 1 into the mixture of A and B boiling under reflux of A, and simultaneously the A formed being removed from the condensate.

To produce Compound B, the process according to the invention is preferably carried out in such a manner that the phosphorus oxychloride is introduced at the rate at which it is consumed into a mixture of dimethylammonium chloride and approximately equal parts by weight of A and B, wherein there are present per mole of phosphorus oxychloride at least 2 moles of dimethylammonium chloride and at least 1 mole of B, the reaction mixture is heated under reflux, until the evolution of hydrogen chloride is practically complete, and subsequently B is obtained from the reaction mixture by fractional distillation.

The Compounds A and B produced according to the process of the invention are valuable intermediate products for the manufacture of pesticides, solvents and lubricants.

EXAMPLE 1

A mixture of 162 g (1 mole) of phosphoric acid-dimethylamide-dichloride, 170 g (1 mole) of phosphoric acid-bis-(dimethylamide)-chloride and 81.5 g (1 mole) of anhydrous dimethylammonium chloride were heated to 120° C. Then, within a period of approximately half an hour, 153.3 g (1 mole) of phosphorus oxychloride were introduced and the reaction mixture was heated under reflux for approximately 5 hours until HCl evolution was complete. Subsequently, all components volatile up to 100° C sump temperature were distilled off at a pressure of 1 mm/Hg without a column.

479.8 g of distillate were obtained, which according to analysis by gas chromatography contained 338.7 g of phosphoric acid dimethylamide-dichloride and 137.2 of phosphoric acid-bis-(dimethylamide)-chloride.

The yield of phosphorus in the distillate, calculated on gram atoms of phosphorus in the starting compounds, was 96.4%, the corresponding yield of nitrogen 92.4%. 150 g of phosphoric acid-dimethylamide-dichloride having a purity of 99.3% were obtained from the distillate by fractionation at 76°/10 torr. The residual amount of phosphoric acid-dimethylamide-dichloride and the total phosphoric acid-bis-(dimethylamide)-chloride were combined with the first distillation residue which still contained some unreacted dimethylammonium chloride and small amounts of phosphoric acid-bis-(dimethylamide)-chloride. This mixture was used again for the production of phosphoric acid-dimethylamide-dichloride.

EXAMPLE 2

90 g (1.11 mole) of anhydrous dimethylammonium chloride and 160 g (0.99 mole) of phosphoric acid-dimethylamide-dichloride were heated under the reflux until the mixture was completely liquid. Then 150 g (0.98 mole) of phosphorus oxychloride were added, the feed rate of which was so controlled that the temperature of the reaction mixture did not fall below 180° C. Subsequently heating under reflux was carried out until the cessation of the HCl evolution. After distillation of the mixture in vacuo at 60° C/1 mm Hg, 305.6 g of phosphoric acid-dimethylamide-dichloride having a purity of 98.5% were obtained. Of this, 160 g were added to the distillation residue as a medium for the next reaction. The yield of phosphoric acid-dimethylamide-dichloride was 92% of the theoretical yield calculated on the phosphorus oxychloride used.

EXAMPLE 3

81.5 g (1 mole) of anhydrous dimethylammonium chloride and 160 g (0.94 mole) of phosphoric acid-bis-(dimethylamide)-chloride were heated to 160° C. 85 g (0.55 mole) of phosphorus oxychloride were then introduced into the clear solution within a period of 5 minutes and the reaction mixture was heated for 7 hours to 190°–210° C. Subsequently, all the components volatile up to 100° C vessel temperature were distilled off at a pressure of 1 mm Hg. 247.2 g of distillate were obtained, which according to analysis by gas chromatography contained 26.2 g of phosphoric acid-dimethylamide-dichloride and 217.5 g of phosphoric acid-bis-(dimethylamide)-chloride. In the distillation residue, there were still 4.7 g of dimethylammonium chloride in the form of constituents insoluble in toluene. The yield of phosphorus (similar to Example 1) was 96.4%, that of nitrogen 96.0°.

There were obtained from the distillate by fractionation at 105°C/10 mm Hg, 205 g of phosphoric acid-bis-(dimethylamide)-chloride having a purity of 98.8% of which 160 grams and the first run (=phosphoric acid-dimethylamide-dichloride) were used as reaction medium for the next mixture.

What is claimed is:

1. A process for the production of phosphoric acid-dimethylamide-dichloride (A) and/or phosphoric acid-bis-(dimethylamide)-chloride (B) by reacting phosphorus oxychloride and dimethylammonium chloride at elevated temperature under anhydrous conditions, which comprises heating phosphorus oxychloride with a mixture of dimethylammonium chloride and at least one of the compounds A and B to temperatures ranging from 130° to 240° C using at least 1 mole dimethylammonium chloride per mole of phosphorus oxychloride.

2. The process according to claim 1, wherein one of the compounds A or B is distilled off the reaction mixture.

3. The process according to claim 1, wherein phosphorus oxychloride is introduced into the reaction mixture in the amount in which it is consumed, and the reaction mixture is heated under reflux.

4. The process according to claim 3, wherein dimethylammonium chloride is introduced into the reaction mixture while it is being refluxed.

5. The process according to claim 1, wherein dimethylammonium chloride is used in molten state.

6. The process according to claim 1, wherein for each part by weight of dimethylammonium chloride, 1.5 – 5 parts by weight of at least one of the compounds A and B is used.

7. The process according to claim 1, wherein a mixture of A and B is used.

8. The process according to claim 7, wherein the mixture of A and B has been obtained by heating dimethylammonium chloride and A.

9. The process according to claim 7, wherein the mixture of A and B has been obtained by heating B and phosphorus oxychloride.

10. The process according to claim 7, wherein approximately equal parts by weight of A and B are used.

11. The process for preparing A according to claim 2, wherein the phosphorus oxychloride is introduced into a mixture of dimethylammonium chloride and approximately equal parts by weight of A and B, wherein at least 1 mole of A is present per mole of phosphorus oxychloride, the reaction mixture is heated under reflux until the evolution of hydrogen chloride is practically complete, and subsequently the A formed is distilled off from the reaction mixture under reduced pressure.

12. The process for preparing B according to claim 2, wherein the phosphorus oxychloride is introduced into a mixture of dimethylammonium chloride and approximately equal parts by weight of A and B, wherein at least 2 moles of dimethylammonium chloride and at least 1 mole of B are present per mole of phosphorus oxychloride, the reaction mixture is heated under reflux until the evolution of hydrogen chloride is practically complete, and subsequently B is obtained from the reaction mixture by fractional distillation.

* * * * *